United States Patent [19]

Van Daalen et al.

[11] 4,174,393

[45] Nov. 13, 1979

[54] 1,3,4-SUBSTITUTED PYRAZOLINE DERIVATIVES

[75] Inventors: Jan J. Van Daalen, Weesp; Rudolf Mulder, Lunteren, both of Netherlands

[73] Assignee: Duphar International Research B.V., Netherlands

[21] Appl. No.: 756,857

[22] Filed: Jan. 5, 1977

Related U.S. Application Data

[63] Continuation-in-part of Ser. No. 594,205, Jul. 9, 1975, Pat. No. 4,070,365.

[30] Foreign Application Priority Data

Jan. 9, 1976 [NL] Netherlands .......................... 7600178

[51] Int. Cl.$^2$ .................... C07D 231/06; A01N 4/12; A01N 9/22; C07D 401/06
[52] U.S. Cl. .................... 424/250; 548/379; 544/371; 544/333; 544/364; 546/211; 546/279; 546/193; 546/194; 424/263; 424/267; 424/273 P
[58] Field of Search ........... 548/379; 424/273, 248.54, 424/248.51, 250, 267, 263; 260/293.7, 294.9, 294.8 E, 268 H, 293 CA; 544/140

[56] References Cited

U.S. PATENT DOCUMENTS

| 4,010,271 | 3/1977 | Mulder et al. ...................... 548/379 |
| 4,070,365 | 1/1978 | Van Daalen et al. ................ 548/379 |

FOREIGN PATENT DOCUMENTS

| 2304584 | 8/1973 | Fed. Rep. of Germany .......... 548/379 |
| 2529689 | 1/1976 | Fed. Rep. of Germany .......... 548/379 |
| 7301203 | 7/1974 | Netherlands ............................. 548/379 |

OTHER PUBLICATIONS

Chemical Abstracts, I, vol. 51, cols. 12887–12888, (1957).
Abstacting Kost et al., "Zhur. Obshchei. Khim.", vol. 27, pp. 258–261, 1722–1726, (1957).
Chemical Abstracts, II, vol. 52, col. 3782, (1958).

*Primary Examiner*—Natalie Trousof
*Assistant Examiner*—Robert T. Bond
*Attorney, Agent, or Firm*—Norman N. Spain

[57] ABSTRACT

The invention relates to novel 1,3,4-substituted-$\Delta^2$-pyrazolines having an insecticidal activity. The compounds are particularly active against larvae of insects for example larvae of Colorado beetle, cabbage white butterfly and yellow-fever mosquito. On the basis of their activity, the compounds, after having been processed to the usual composition, may be used in controlling insects, particularly in the field of agriculture and horticulture. The dosage is 0.05 –1 kg of the active substance per hectare.

18 Claims, No Drawings

1,3,4-SUBSTITUTED PYRAZOLINE DERIVATIVES

This application is a continuation-in-part of copending Application Ser. No. 594,205, filed July 9, 1975 and now U.S. Pat. No. 4,070,365.

It is known from German Offenlegungsschrift No. 2,304,584 in the name of Applicants that pyrazoline compounds which in the 1,3 or 1,3,5 positions of the pyrazoline ring are provided with a substituent, exert a biocidal activity with respect to arthropods, for example, mites and insects.

It has now been found that new pyrazoline compounds which satisfy the formula below and which, as may be read from the formula, contain substituents in the 1, 3 and 4 positions of the pyrazoline ring, have a very strong insecticidal activity.

The compounds according to the present invention may be represented by the formula

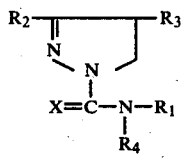

in which $R_1$ is an alkyl group, a cyclo alkyl group, a phenyl alkyl group of which the phenyl nucleus may be substituted with halogen, alkyl or nitro, a heterocyclic ring which contains 1-2 nitrogen atoms and may be substituted with halogen, alkyl or nitro, a phenyl group or a phenyl group which is substituted in the 2, 3 or 4 positions with 1 to 2 substituents selected from the group consisting of halogen, alkyl, halogenalkyl, cycloalkyl, alkylthio, alkoxy, dialkylamino, alkylsulphonyl, acyl, acylamino, cyano, nitro, phenyl, halophenyl, phenylthio, phenoxy, and phenylalkyl radical, $R_2$ is an alkyl group, a cycloalkyl group, a pyridyl group or a thienyl group which may be substituted with halogen, alkyl or nitro, a phenyl group or a phenyl group substituted with 1 to 2 substituents selected from the group consisting of halogen, alkyl, haloalkyl, cycloalkyl, alkylthio, alkoxy, mono- or dialkylamino, nitro, phenyl, halophenyl and cyano, $R_4$ is a hydrogen atom, an alkyl group having 1-15 carbon atoms, a phenylalkyl group, a cycloalkyl group or a halomethylthio group; $R_3$ is an alkyl group having 5-10 carbon atoms, an alkyl group having 1-6 carbon atoms which is substituted by cycloalkyl; alkoxy; alkylthio; nitro; halogen; cyano; alkoxycarbonyl; optionally by nitro, halogen or alkyl substituted phenyl, phenoxy, phenylthio, phenylsulphinyl or phenylsulphonyl; dialkylamino the alkyl groups of which may form together with the nitrogen atom to which they are bound a saturated or unsaturated, optionally substituted heterocyclic ring which may contain a second hetero atom; alkylphenyl- or diphenylamino; N,N-dialkylcarbamoyl, N,N-dialkylsulphomoyl; on the understanding that when $R_1$ is a phenyl group substituted by phenylthio, phenoxy or phenylalkyl and/or $R_4$ is a phenylalkyl, cycloalkyl, or halogenmethylthio group, only in such a case $R_3$ may also have a meaning mentioned for $R_2$; and X is an oxygen atom or a sulphur atom.

Structurally related 1,3,4-substituted pyrazoline derivatives are the subject matter of Netherlands Patent Application No. 74.09433 filed in the Netherlands July 12, 1974 corresponding to U.S. Pat. Application Ser. No. 594,205 filed Aug. 9, 1975 and now U.S. Pat. No. 4,070,365. The compounds described in said Application also have good insecticidal properties.

If an alkyl group, phenylalkyl group, alkylthio group, alkoxy group, alkylamino group, dialkylamino group or an alkylsulphenyl group occurs in the substituents $R_1-R_4$, then the alkyl radical present in such group contains 1-4 carbon atoms; and in the case where as cyclo-alkyl group occurs the cycloalkyl group represented by $R_1$ to $R_4$ contains 3-6 carbon atoms.

If an acylgroup or an acylamino group occurs in $R_1$, then the acyl part of such a group is preferably derived from an aliphatic monocarboxylic acid, for example acetic acid or propionic acid.

When $R_1$ represents a heterocyclic ring which contains 1 to 2 nitrogen atoms, this is preferably a pyridine or pyrimidine ring.

It has been found by biological evaluation examination that the compounds according to the invention have a good insecticidal activity and, already at low dosages, they are capable of controlling, for example, beetles, larvae of beetles, larvae of mosquitoes as well as caterpillars.

It has surprisingly been found that the insecticidal activity of the compounds according to the invention is considerably better than that of the known 1,3- and 1,3,5-substituted pyrazolines. It has been found that in many cases the substances according to the invention also have a good activity against the yellow fever mosquito in addition to an excellent activity against both the Colorado beetle and the caterpillar. Compounds from the known series of 1,3,5-substituted pyrazolines and 1,3-substituted compounds there is often found, apart from a good activity against larvae of the Colorado beetle, a less strong activity against the larvae of the Cobbage white butterfly and in general no or substantially no activity against larvae of the yellow-fever mosquito.

Many of the active substances according to the invention show, for example, an optimal activity in a concentration of 0.3-3 ppm show against the larvae of the Colorado beetle, and in a concentration of 0.3-30 ppm show a maximum activity against the caterpillar and furthermore in a concentration of 0.03-0.3 ppm show a maximum activity against larvae of the yellow-fever mosquito. The following active substances are particularly suitable:

(1) 1-phenylcarbamoyl-3-(4-chlorophenyl)-4-(2-methyl-2-nitropropyl)-2-pyrazoline, m.p. 146° C.;

(2) 1-(3-trifluoromethylphenylcarbamoyl)-3-(4-chlorophenyl)-4-(2-methyl-2-nitropropyl)-2-pyrazoline, m.p. 160° C. (decomposition);

(3) 1-(3-nitro-4-methoxyphenylcarbamoyl)-3-(4-chlorophenyl)-4-(2-methyl-2-nitropropyl)-2-pyrazoline, m.p. 198° C.;

(4) 1-(4-chlorophenylcarbamoyl)-3-(4-chlorophenyl)-4-(2-methyl-2-nitropropyl)-2-pyrazoline, m.p. 219° C. (decomposition);

(5) 1-(4-chlorophenylcarbamoyl)-3-(4-chlorophenyl)-4-n-heptyl-2-pyrazoline, m.p. 135° C.;

(6) 1-(4-n-propylphenylcarbamoyl)-3-(4-chlorophenyl)-4-n-heptyl-2-pyrazoline, m.p. 111° C.;

(7) 1-(4-methoxyphenylcarbamoyl)-3-(4-chlorophenyl)-4-n-heptyl-2-pyrazoline, m.p. 117° C.;

(8) 1-cyclohexylcarbamoyl-3-(4-chlorophenyl)-4-n-heptyl-2-pyrazoline, m.p. 107° C.;

(9) 1-n-butylcarbamoyl-3-(4-chlorophenyl)-4-n-heptyl-2-pyrazoline, m.p. 30° C.;

(10) 1-(4-methylthiophenylcarbamoyl)-3-(4-chlorophenyl)-4-n-heptyl-2-pyrazoline, m.p. 115° C.;
(11) 1-(3,4-di-chlorophenylcarbamoyl)-3-(4-chlorophenyl)-4-n-heptyl-2-pyrazoline, m.p. 111° C.;
(12) 1-(4-nitrophenylcarbamoyl)-3-(4-chlorophenyl)-4-n-heptyl-2-pyrazoline, m.p. 119° C.;
(13) 1-(4-cyanophenylcarbamoyl)-3-(4-chlorophenyl)-4-n-heptyl-2-pyrazoline, m.p. 144° C.;
(14) 1-(4-chlorophenylcarbamoyl)-3-(4-chlorophenyl)-4-n-decyl-2-pyrazoline, m.p. 113° C.;
(15) 1-(4-cyanophenylcarbamoyl)-3-(4-chlorophenyl)-4-n-decyl-2-pyrazoline, m.p. 114° C.;
(16) 1-(4-nitrophenylcarbamoyl)-3-(4-chlorophenyl)-4-n-decyl-2-pyrazoline, m.p. 107° C.;
(17) 1-(4-methoxyphenylcarbamoyl)-3-(4-chlorophenyl)-4-n-decyl-2-pyrazoline, m.p. 105° C.;
(18) 1-(4-methylthiophenylcarbamoyl)-3-(4-chlorophenyl)-4-n-decyl-2-pyrazoline, m.p. 122° C.;
(19) 1-(4-n-propylphenylcarbamoyl)-3-(4-chlorophenyl)-4-n-decyl-2-pyrazoline, m.p. 125° C.;
(20) 1-cyclohexylcarbamoyl-3-(4-chlorophenyl)-4-n-decyl-2-pyrazoline. m.p. 87° C.;
(21) 1-(4-chlorophenylcarbamoyl)-3-(4-chlorophenyl)-4-(2-methoxyethyl)-2-pyrazoline, m.p. 87° C.;
(22) 1-(4-ethoxyphenylcarbamoyl)-3-(4-chlorophenyl)-4-(2-methoxyethyl)-2-pyrazoline, m.p. 111° C.;
(23) 1-(4-methylthiophenylcarbamoyl)-3-(4-chlorophenyl)-4-(2-methoxyethyl)-2-pyrazoline, m.p. 83° C.;
(24) 1-(4-nitrophenylcarbamoyl)-3-(4-chlorophenyl)-4-(2-methoxyethyl)-2-pyrazoline, m.p. 159° C.;
(25) 1-cyclohexylcarbamoyl-3-(4-chlorophenyl)-4-(2-methoxyethyl)-2-pyrazoline, m.p. 104° C.;
(26) 1-cyclohexylcarbamoyl-3-(4-chlorophenyl)-4-(2-piperidino-ethyl)-2-pyrazoline, m.p. 113° C.;
(27) 1-(4-cyanophenylcarbamoyl)-3-(4-chlorophenyl)-4-(2-piperidinoethyl)-2-pyrazoline, m.p. 148° C.;
(28) 1-(4-isopropoxyphenylcarbamoyl)-3-(4-chlorophenyl)-4-(2-piperidinoethyl)-2-pyrazoline, m.p. 113° C.;
(29) 1-(4-ethylphenylcarbamoyl)-3-(4-chlorophenyl)-4-(2-piperidinoethyl)-2-pyrazoline, m.p. 111° C.;
(30) 1-(4-chlorophenylcarbamoyl)-3-(4-chlorophenyl)-4-(2-piperidinoethyl)-2-pyrazoline, m.p. 134° C.;
(31) 1-(4-chlorophenylcarbamoyl)-3-(4-chlorophenyl)-4-(2-diethylaminoethyl)-2-pyrazoline, m.p. 100° C.;
(32) 1-(4-ethylphenylcarbamoyl)-3-(4-chlorophenyl)-4-(2-diethylaminoethyl)-2-pyrazoline;
(33) 1-(4-isopropoxyphenylcarbamoyl)-3-(4-chlorophenyl)-4-(2-diethylaminoethyl)-2-pyrazoline;
(34) 1-(4-cyanophenylcarbamoyl)-3-(4-chlorophenyl)-4-(2-diethylaminoethyl)-2-pyrazoline;
(35) 1-cyclohexylcarbamoyl-3-(4-chlorophenyl)-4-(2-diethylamonoethyl)-2-pyrazoline, m.p. 87° C.;
(36) 1-[N-(4-chlorophenyl)-N-methylcarbamoyl]-3-(4-chloropyenyl)-4-(2-piperidinoethyl)-2-pyrazoline;
(37) 1-(4-chlorophenylcarbamoyl)-3-(4-chlorophenyl)-4-(2-phenylthioethyl)-2-pyrazoline, m.p. 137° C.;
(38) 1-(4-isopropoxyphenylcarbamoyl)-3-(4-chlorophenyl)-4-(2-phenylthioethyl)-2-pyrazoline, m.p. 138° C.;
(39) 1-(4-methylthiophenylcarbamoyl)-3-(4-chlorophenyl)-4-(2-phenylthioethyl)-2-pyrazoline, m.p. 124° C.;
(40) 1-(4-ethylphenylcarbamoyl)-3-(4-chlorophenyl)-4-(2-phenylthioethyl)-2-pyrazoline, m.p. 122° C.;
(41) 1-(4-fluorophenylcarbamoyl)-3-(4-chlorophenyl)-4-(2-phenylthioethyl)-2-pyrazoline, m.p. 130° C.;
(42) 1-(4-isopropoxyphenylcarbamoyl)-4-(4-chlorophenyl)-4-(2-phenoxyethyl)-2-pyrazoline, m.p. 100° C.;
(43) 1-(4-methylthiophenylcarbamoyl)-3-(4-chlorophenyl)-4-(2-phenoxyethyl)-2-pyrazoline, m.p. 112° C.;
(44) 1-(4-benzylphenylcarbamoyl)-3-(4-chlorophenyl)-4-phenyl-2-pyrazoline, m.p. 179° C.;
(45) 1-(4-phenylthiophenylcarbamoyl)-3-(4-chlorophenyl)-4-phenyl-2-pyrazoline, m.p. 164° C.;
(46) 1-(4-phenoxyphenylcarbamoyl)-3-(4-chlorophenyl)-4-phenyl-2-pyrazoline, m.p. 177° C.;
(47) 1-[N-(1-chlorophenyl)-N-(trichloromethylthio)-carbamoyl]-3-(4-chlorophenyl)-4-phenyl-2-pyrazoline, m.p. 177° C.;
(48) 1-[N-benyl-N-(4-chlorophenyl)-carbamoyl]-3-(4-chlorophenyl)-4-phenyl-2-pyrazoline, m.p. 116° C.;
(49) 1-[N-cyclohexyl-N-(4-chlorophenyl)-carbamoyl]-3-(4-chlorophenyl)-4-phenyl-2-pyrazoline, m.p. 138° C.;
(50) 1-phenylcarbamoyl-3-(4-chlorophenyl)-4-cyclohexylmethyl-2-pyrazoline, m.p. 179° C.;
(51) 1-(4-chlorophenylcarbamoyl)-3-(4-chlorophenyl)-4-cyclohexylmethyl-2-pyrazoline, m.p. 153° C.;
(52) 1-(4-isopropoxyphenylcarbamoyl)-3-(4-chlorophenyl)-4-cyclohexylmethyl-2-pyrazoline, m.p. 123° C.;
(53) 1-(4-cyanophenylcarbamoyl)-3-(4-chlorophenyl)-4-cyclohexylmethyl-2-pyrazoline, m.p. 173° C.;
(54) 1-(4-nitrophenylcarbamoyl)-3-(4-chlorophenyl)-4-cyclohexylmethyl-2-pyrazoline, m.p. 228° C.;
(55) 1-(4-ethylphenylcarbamoyl)-3-(4-chlorophenyl)-4-cyclohexylmethyl-2-pyrazoline, m.p. 131° C.;
(56) 1-cyclohexylcarbamoyl-3-(4-chlorophenyl)-4-cyclohexylmethyl-2-pyrazoline, m.p. 169° C.;
(57) 1-(4-chlorophenylcarbamoyl)-3-(4-methoxyphenyl)-4-β-phenylethyl-2-pyrazoline, m.p. 143° C.;
(58) 1-(4-ethylphenylcarbamoyl)-3-(4-methoxyphenyl)-4-β-phenylenthyl-2-pyrazoline, m.p. 111° C.;
(59) 1-(4-isopropoxyphenylcarbamoyl)-3-(4-methoxyphenyl)-4-β-phenylethyl-2-pyrazoline, m.p. 110° C.;
(60) 1-(4-cyanophenylcarbamoyl)-3-(4-methoxyphenyl)-4-β-phenylethyl-2-pyrazoline, m.p. 142° C.;
(61) 1-(nitrophenylcarbamoyl)-3-(4-methoxyphenyl)-4-β-phenylethyl-2-pyrazoline, m.p. 158° C.;
(62) 1-cyclohexylcarbamoyl-3-(4-methoxyphenyl)-4-β-phenylethyl-2-pyrazoline, m.p. 126° C.;
(63) 1-(4-chlorophenylcarbamoyl)-3-(4-isopropoxyphenyl)-4-β-diethylaminoethyl-2-pyrazoline;
(64) 1-(4-nitrophenylcarbamoyl)-3-(4-isopropoxyphenyl)-4-β-diethylaminoethyl-2-pyrazoline;
(65) 1-phenylcarbamoyl-3-(4-isopropoxyphenyl)-4-β-diethylaminoethyl-2-pyrazoline;
(66) 1-(4-isopropoxyphenylcarbamoyl)-3-(4-isopropoxyphenyl)-4-β-diethylaminoethyl-2-pyrazoline;
(67) 1-(4-isopropylphenylcarbamoyl)-3-(4-isopropoxyphenyl)-4-β-diethylaminoethyl-2-pyrazoline;
(68) 1-cyclohexylcarbamoyl-3-(4-isopropoxyphenyl)-4-β-diethylaminoethyl-2-pyrazoline;
(69) 1-(4-chlorophenylcarbamoyl)-3-(4-chlorophenyl)-4-[β-(N-methylpiperazino)-ethyl]-2-pyrazoline, m.p. 159° C.;
(70) 1-(4-methoxyphenylcarbamoyl)-3-(4-chlorophenyl)-4-[β-(N-methylpiperazine)-ethyl]-2-pyrazoline, m.p. 173° C.;
(71) 1-(4-methylphenylcarbamoyl)-3-(4-chlorophenyl)-4-[β-(N-methylpiperazino)-ethyl]-2-pyrazoline, m.p. 159° C.;

(72) 1-(4-isobutylphenylcarbamoyl)-3-(4-chlorophenyl)-4-[β-(N-methylpiperazino)-ethyl]-2-pyrazoline, m.p. 136° C.;
(73) 1-cyclohexylcarbamoyl-3-(4-chlorophenyl)-4-[β-(N-methylpiperazino)-ethyl]-2-pyrazoline;
(74) 1-(4-chlorophenylcarbamoyl)-3-(4-chlorophenyl)-4-benzyl-2-pyrazoline, m.p. 145° C.;
(75) 1-(4-methoxyphenylcarbamoyl)-3-(4-chlorophenyl)-4-benzyl-2-pyrazoline, m.p. 141° C.;
(76) 1-(4-ethylphenylcarbamoyl)-3-(4-chlorophenyl)-4-benzyl-2-pyrazoline, m.p. 95° C.;
(77) 1-(4-cyanophenylcarbamoyl)-3-(4-chlorophenyl)-4-benzyl-2-pyrazoline, m.p. 184° C.;
(78) 1-cyclohexylcarbamoyl-3-(4-chlorophenyl)-4-benzyl-2-pyrazoline, m.p. 126° C.;
(79) 1-(4-chlorophenylcarbamoyl)-3-(4-chlorphenyl)-4-β-phenylsulfonethyl-2-pyrazoline, m.p. 203° C.;
(80) 1-(4-cyanophenylcarbamoyl)-3-(4-chlorophenyl)-4-β-phenylsulfonethyl-2-pyrazoline, m.p. 181° C.;
(81) 1-cyclohexylcarbamoyl-3-(4-chlorophenyl)-4-β-phenylsulfonethyl-2-pyrazoline, m.p. 194° C.;
(82) 1-(4-methylphenylcarbamoyl)-3-(4-chlorophenyl)-4-β-phenylsulfonethyl-2-pyrazoline, m.p. 210° C.;
(83) 1-phenylcarbamoyl-3-(4-chlorophenyl)-4-β-phenylsulfonethyl-2-pyrazoline, m.p. 168° C.;
(84) 1-(4-isopropoxyphenylcarbamoyl)-3-(4-chlorophenyl)-4-β-phenylsulfonethyl-2-pyrazoline, m.p. 168° C.;
(85) 1-(4-isobutylphenylcarbamoyl)-3-(4-chlorophenyl)-4-β-phenylsulfonethyl-2-pyrazoline, m.p. 156° C.;
(86) 1-(3-trifluoromethylphenylcarbamoyl)-3-(4-chlorophenyl)-4-β-phenylsulfonethyl-2-pyrazoline, m.p. 180° C.;
(87) 1-(3-chloro-4-methoxyphenylcarbamoyl)-3-(4-chlorophenyl)-4-β-phenylsulfonethyl-2-pyrazoline, m.p. 120° C.;
(88) 1-(4-chlorophenylcarbamoyl)-3-(4-chlorophenyl)-4-(3-carbethoxypropyl)-2-pyrazoline, m.p. 135° C.;
(89) 1-(4-isopropoxyphenylcarbamoyl)-3-(4-chlorophenyl)-4-(3-carbethoxypropyl)-2-pyrazoline, m.p. 97° C.;
(90) 1-(4-methylphenylcarbamoyl)-3-(4-chlorophenyl)-4-(3-carbethoxypropyl)-2-pyrazoline, m.p. 88° C.;
(91) 1-(4-chlorophenylcarbamoyl)-3-(4-chlorophenyl)-4-[3-(dimethylcarbamoyl)-propyl]-2-pyrazoline, m.p. 136° C.;
(92) 1-(4-isopropoxyphenylcarbamoyl)-3-(4-chlorophenyl)-4-[3-(dimethylcarbamoyl)-propyl]-2-pyrazoline, m.p. 158° C.;
(93) 1-(4-ethylphenylcarbamoyl)-3-(4-chlorophenyl)-4-[3-(dimethylcarbamoyl)-propyl]-2-pyrazoline, m.p. 145° C.;
(94) 1-(3,4-dichlorophenylcarbamoyl)-3-(4-chlorophenyl)-4-[3-(dimethylcarbamoyl)-propyl]-2-pyrazoline, m.p. 169° C.;
(95) 1-(4-methoxyphenylcarbamoyl)-3-(4-chlorophenyl)-4-(3-methoxypropyl)-2-pyrazoline, m.p. 122° C.;
(96) 1-(4-chlorophenylcarbamoyl)-3-(4-chlorophenyl)-4-(3-methoxypropyl)-2-pyrazoline, m.p. 127° C.;
(97) 1-(4-methylthiophenylcarbamoyl)-3-(4-chlorophenyl)-4-(3-methoxypropyl)-2-pyrazoline, m.p. 124° C.;
(98) 1-cyclohexylcarbamoyl-3-(4-chlorophenyl)-4-(3-methoxy-propyl)-2-pyrazoline, m.p. 97° C.;
(99) 1-(4-cyanophenylcarbamoyl)-3-(4-chlorophenyl)-4-(3-methoxypropyl)-2-pyrazoline, m.p. 190° C.;
(100) 1-(4-nitrophenylcarbamoyl)-3-(4-chlorophenyl)-4-(3-methoxypropyl)-2-pyrazoline. m.p. 143° C.;
(101) 1-(4-chlorophenylcarbamoyl)-3-(4-chlorophenyl)-4-3-piperidinopropyl)-2-pyrazoline, m.p. 107° C.;
(102) 1-(4-cyanophenylcarbamoyl)-3-(4-chlorophenyl)-4-(3-piperidinopropyl)-2-pyrazoline, m.p. 120° C.;
(103) 1-(4-chlorophenylcarbamoyl)-3-(4-chlorophenyl)-4-cyanomethyl-2-pyrazoline, m.p. 175° C.;
(104) 1-(4-cyanophenylcarbamoyl)-3-(4-chlorophenyl)-4-cyanomethyl-2-pyrazoline, m.p. 205° C.;
(105) 1-(4-isopropylphenylcarbamoyl)-3-(4-chlorophenyl)-4-cyanomethyl-2-pyrazoline, m.p. 157° C.;
(106) 1-(4-methoxyphenylcarbamoyl)-3-(4-chlorophenyl)-4-cyanomethyl-2-pyrazoline, m.p. 205° C.;
(107) 1-cyclohexylcarbamoyl-3-(4-chlorophenyl)-4-cyanomethyl-2-pyrazoline, m.p. 170° C.;
(108) 1-(4-chlorophenylcarbamoyl)-3-(4-chlorophenyl)-4-(β-ethylthioethyl)-2-pyrazoline, m.p. 102° C.;
(109) 1-(4-methoxyphenylcarbamoyl)-3-(4-chlorophenyl)-4-(β-ethylthioethyl)-2-pyrazoline, m.p. 83° C.;
(110) 1-(4-methylthiophenylcarbamoyl)-3-(4-chlorophenyl)-4-(β-ethylthioethyl)-2-pyrazoline, m.p. 111° C.;
(111) 1-(4-cyanophenylcarbamoyl)-3-(4-chlorophenyl)-4-(β-ethylthioethyl)-2-pyrazoline, m.p. 190° C.;
(112) 1-cyclohexylcarbamoyl-3-(4-chlorophenyl)-4-(β-ethylthioethyl)-2-pyrazoline, m.p. 98° C.;
(113) 1-(4-chlorophenylcarbamoyl)-3-(4-chlorophenyl)-4-(β-dimethylaminoethyl)-2-pyrazoline, m.p. 131° C.;
(114) 1-(4-cyanophenylcarbamoyl)-3-(4-chlorophenyl)-4-(β-dimethylaminoethyl)-2-pyrazoline, m.p. 175° C.;
(115) 1-cyclohexylcarbamoyl-3-(4-chlorophenyl)-4-(β-dimethylaminoethyl)-2-pyrazoline, m.p. 115° C.;
(116) 1-(4-methylthiopenylcarbamoyl)-3-(4-chlorophenyl)-4-(β-dimethylaminoethyl)-2-pyrazoline, m.p. 117° C.;
(117) 1-(4-methoxyphenylcarbamoyl)-3-(4-chlorophenyl)-4-(β-dimethylaminoethyl)-2-pyrazoline, m.p. 103° C.;
(118) 1-(4-isopropylphenylcarbamoyl)-3-(4-chlorophenyl)-4-(β-dimethylaminoethyl)-2-pyrazoline, m-p. 157° C.;
(119) 1-(4-chlorophenylcarbamoyl)-3-(4-chlorophenyl)-4-carbethoxymethyl-2-pyrazoline, m.p. 114° C.;
(120) 1-phenylcarbamoyl-3-(4-chlorophenyl)-4-carbethoxymethyl-2-pyrazoline, m.p. 98° C.;
(121) 1-(4-ethylphenylcarbamoyl)-3-(4-chlorophenyl)-4-carbethoxymethyl-2-pyrazoline, m.p. 113° C.;
(122) 1-(4-isobutylphenylcarbamoyl)-3-(4-chlorophenyl)-4-carbethoxymethyl-2-pyrazoline, m.p. 123° C.;
(123) 1-(4-isopropoxyphenylcarbamoyl)-3-(4-chlorophenyl)-4-carbethoxymethyl-2-pyrazoline, m.p. 96° C.;
(124) 1-(4-methoxyphenylcarbamoyl)-3-(4-chlorophenyl)-4-carbethoxymethyl-2-pyrazoline, m.p. 85° C.;
(125) 1-(3,4-dichlorophenylcarbamoyl)-3-(4-chlorophenyl)-4-carbethoxymethyl-2-pyrazoline, m.p. 125° C.;
(126) 1-(4-cyanophenylcarbamoyl)-3-(4-chlorophenyl)-4-carbethoxymethyl-2-pyrazoline, m.p. 159° C.;
(127) 1-(4-chlorophenylcarbamoyl)-3-(4-chlorophenyl)-4-3-ethylthiopropyl)-2-pyrazoline, m.p. 105° C.;
(128) 1-(4-cyanophenylcarbamoyl)-3-(4-chlorophenyl)-4-(3-ethylthiopropyl)-2-pyrazoline, m.p. 130° C.;

(129) 1-(4-ethylphenylcarbamoyl)-3-(chlorophenyl)-4-3-ethylthiopropyl)-2-pyrazoline, m.p. 87° C.;

(130) 1-(4-methoxyphenylcarbamoyl)-3-(4-chlorophenyl)-4-(3-ethylthiopropyl)-2-pyrazoline, m.p. 86° C.;

(131) 1-(4-methylthiophenylcarbamoyl)-3-(4-trifluoromethylphenyl)-4-(3-methoxypropyl)-2-pyrazoline, m.p. 97° C.;

(132) 1-(4-chlorophenylcarbamoyl)-3-(4-trifluoromethylphenyl)-4-(3-methoxypropyl)-2-pyrazoline, m.p. 97° C.;

(133) 1-(4-ethoxyphenylcarbamoyl)-3-(4-trifluoromethylphenyl)-4-(3-methoxypropyl)-2-pyrazoline, m.p. 105° C.;

(134) 1-(4-cyanophenylcrbamoyl)-3-(4-trifluoromethylphenyl)-4-(3-methoxypropyl)-2-pyrazoline, m.p. 152° C.;

(135) 1-(4-isobutylphenylcarbamoyl)-3-(4-trifluoromethylphenyl)-4-(3-methoxypropyl)-2-pyrazoline, m.p. 110° C.;

(136) 1-(4-fluorophenylcarbamoyl)-3-(4-trifluoromethylphenyl)-4-(3-methoxypropyl)-2-pyrazoline, m.p. 113° C.;

(137) 1-(4-methoxyphenylcarbamoyl)-3-(4-chlorophenyl)-4-(3-cyanopropyl)-2-pyrazoline, m.p. 126° C.;

(138) 1-(4-methylthiophenylcarbamoyl)-3-(4-chlorophenyl)-4-(3-cyanopropyl)-2-pyrazoline, m.p. 109° C.;

(139) 1-phenylcarbamoyl-3-(4-chlorophenyl)-4-(3-cyanopropyl)-2-pyrazoline, m.p. 148° C.;

(140) 1-(4-chlorophenylcarbamoyl)-3-(chlorophenyl)-4-(3-cyanopropyl)-2-pyrazoline, m.p. 120° C.;

(141) 1-(4-isopropylphenylcarbamoyl)-3-(4-chlorophenyl)-4-(3-cyanopropyl)-2-pyrazoline, m.p. 154° C.;

(142) 1-(4-fluorophenylcarbamoyl)-3-(4-chlorophenyl)-4-benzyl-2-pyrazoline, m.p. 130° C.;

(143) 1-(4-nitrophenylcarbamoyl)-3-(4-chlorophenyl)-4-benzyl-2-pyrazoline, m.p. 167° C.;

(144) 1-(4-chlorophenylcarbamoyl)-3-(4-chlorophenyl)-4-(dimethylcarbamoylmethyl)-2-pyrazoline, m.p. 151° C.;

(145) 1-phenylcarbamoyl-3-(4-chlorophenyl)-4-(dimethylcarbamoylmethyl)-2-pyrazoline, m.p. 145° C.;

(146) 1-(4-ethylphenylcarbamoyl)-3-(4-chlorophenyl)-4-(dimethylcarbamoylmethyl)-2-pyrazoline, m.p. 155° C.;

(147) 1-(4-methoxyphenylcarbamoyl)-3-(4-chlorophenyl)-4-(dimethylcarbamoylmethyl)-2-pyrazoline, m.p. 151° C.;

(148) 1-(4-cyanophenylcarbamoyl)-3-(4-chlorophenyl)-4-(dimethylcarbamoylmethyl)-2-pyrazoline, m.p. 210° C.;

In particular the compounds of the above general formula, in which $R_3$ is an alkyl radical having 1 to 6 carbon atoms which is substituted with an alkoxy group having 1 to 4 carbon atoms or a dialkylamino group of which the alkyl radicals together with the nitrogen atom to which they are bound can form a heterocyclic ring, show very strong insecticidal properties.

In addition to the strong insecticidal activity it has been found that the compounds of the above general formula, in which $R_1$, $R_2$ and $R_4$ have the above meanings, and $R_3$ is an alkyl group having 1 to 6 carbon atoms which is substituted with a cyano group or a dialkylamino group, which two alkyl radicals can form—with the nitrogen atom to which they are bound—a possibly alkylated heterocyclic ring which may comprise a second hetero atom, also show fungicidal properties.

On the basis of their strong insecticidal activity the substances according to the invention may be used in low dosages in controlling insects. The amount of the dosage depends on a variety of factors, for example, the substance used, the kind of insect, the formulation used, the state of the crop infected with insects, and the prevailing weather conditions. In general, for the control of insects in agriculture and horticulture a dosage corresponding to 0.05–1 kg of the active substance per hectare yields good results.

For practical application, the compounds according to the invention are processed to compositions. In these compositions the active substance is mixed with solid carrier material or dissolved or dispersed in a liquid carrier material, if desired combined with auxiliary substances, for example surface-active substances and stabilizers.

Examples of compositions according to the invention are aqueous solutions and dispersions, oily solutions and oil dispersions, pastes, dusting powders, wettable powders, miscible oils, granules, invert emulsions, aerosol compositions and fumigating candles.

Wettable powders, pastes and miscible oils are compositions in concentrated form which are diluted with water prior to or during use.

The invert emulsions are mainly used in air applications, namely when large areas are treated with a comparatively small quantity of composition. The invert emulsions can be prepared shortly before or even during the spraying in the spraying apparatus by emulsifying water in an oily solution or an oily dispersion of the active substance. Some types of compositions will be described in greater detail hereinafter by way of example.

Granular compositions are prepared, for example, by taking up the active substance in a solvent and impregnating the resulting solution, optionally in the presence of a binder, on granular carrier material, for example porous granules (for example pumice and attaclay), mineral non-porous granules (sand or ground marl), organic granules (for example dried coffee grounds and cut tobacco stems).

A granular composition can also be prepared by compressing the active substance together with powdered minerals in the presence of lubricating agents and binders and to disintegrate and sieve the compressed product to the desired grain size.

Dusting powders can be obtained by intimately mixing the active substance with an inert solid carrier material, for example in a concentration of 1 to 50% by weight. As examples of suitable solid carrier materials may be mentioned talc, kaolin, pipe clay, diatomaceous earth, dolomite, gypsum, chalk, bentonite, attapulgite and colloidal $SiO_2$ or mixtures of these and similar substances. Organic carrier materials, for example, ground sheels of walnuts may also be used.

Wettable powders are prepared by mixing 1 to 80 parts by weight of a solid inert carrier, for example the above-mentioned carrier materials, with 10 to 80 parts by weight of the active substance, 1 to 5 parts by weight of a dispersion agent, for example the lignine sulphonates or alkylnaphthalene sulphonates known for this purpose, and preferably also 0.5 to 5 parts by weight of a setting agent, for example, sulphates of aliphatic alcohol, alkylarylsulphonates or fatty acid condensation products.

For the preparation of miscible oils the active compound is dissolved or finely divided in a suitable solvent which preferably is poorly water-miscible and an emulsifier is added to this solution. Suitable solvents are, for example, xylene, toluene, petroleum distillates which are rich in aromatices, for example, solvent natphtha, distilled tar oil and mixtures of these liquids. As emulsifiers may be used for example, alkylphenoxy polyglycol ethers, polyoxyethylene sorbitan esters of fatty acids or polyoxyethylene sorbitol esters of fatty acids. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example acetone, to which solution a dispersion agent and possibly a wetting agent have been added. An aqueous dispersion of the active substance is obtained upon diluting with water shortly before or during spraying.

An aerosol composition according to the invention is obtained in the usual manner by incorporating the active substance, optionally in a solvent, in a volatile liquid to be used as a propellant, for example a mixture of chloro-fluoro-derivatives of methane and ethane.

Fumigating candles or fumigating powders, that is compositions which can generate a pesticidal smoke while burning, are obtained by taking up the active substance in a combustible mixture which may contain, for example, as a fuel, a sugar or wood, preferably in a groundform, a substance to maintain the combustion, for example, ammonium nitrate or potassium chlorate, and in addition a substance to delay the combustion, for example, kaolin, bentonite and/or colloidal silica.

In addition to the above-mentioned ingredients, the compositions according to the invention may also contain other substances known for application in this kind of compositions.

For example, a lubricant such as calcium stearate or magnesium stearate, may be added to a wettable powder or a mixture to be granulated. "Adhesives" for example, polyvinyl alcohol and cellylose derivatives or other colloidal materials, such as casein, may also be added to improve the adhesion of the pesticidal composition to the surface to be protected.

Known pesticidal compounds may also be incorporated in the compositions according to the invention. As a result of this the activity spectrum of the compositions is broadened and synergism may occur.

The following known insecticidal, fungicidal and acaricidal compounds are suitable for use in such combination compositions:

INSECTICIDES SUCH AS:

1. chlorinated hydrocarbons, for example, 2,2-bis-(p-chlorophenyl)-1,1,1-trichloroethane and hexachloroepoxyoctahydro-dimethanonaphthalene;
2. carbamates, for example, N-methyl-1-naphthylcarbamate;
3. dinitrophenols, for example 2-methyl-4,6-dinitrophenol and 2-(2-butyl)-4,6-dinitrophenyl)-3,3-dimethylacrylate;
4. organic phosphorus compounds, for example dimethyl-2-methoxy-carbonyl-2-methylvinyl-phosphate; O,O-diethyl-O-p.nitrophenyl-phosphorthioate; N-monomethylamide of O,O-dimethyldithiophosphoryl acetic acid;

ACARICIDES, FOR EXAMPLE:

5. diphenylsulfides, for example p-chlorobenzyl-p-chlorophenylsulfide and 2,4,4',5-tetrachlorodiphenylsulfide;
6. diphenylsulphonates, for example p-chlorophenyl benzene sulphonates;
7. methylcarbinols, for example 4,4-dichloro-a-trichloromethylbenzhydrol;
8. quinoxaline compounds for example methylquinoxaline dithiocarbonate.

FUNGICIDES, FOR EXAMPLE:

9. organic mercury compounds, for example phenyl mercury acetic and methyl mercury cyanoguanide;
10. organic tin compounds, for example triphenyltin hydroxide and triphenyltin acetate;
11. alkylene bis-dithiocarbamates, for example, zinc ethylene bis- dithiocarbamate and manganese ethylene bis-dithiocarbamate; and
12. 2,4-dinitro-6-(2-octyl-phenyl-crotonate), 1-bis(-dimethylamino)phosphoryl-3-phenyl-5-amino-1,2,4-triazol-6-methyl-quinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichloro-fluoromethylthio-N-phenyl-N'-dimethyl-sulphonyldiamide and tetrachloroisophthalonitrile.

As already noted above the active compounds according to the present invention are novel substances which can be prepared according to methods which are known per se for the synthesis of similar substances or methods analogous thereto.

For example the substances can be prepared by reacting a compound of the formula

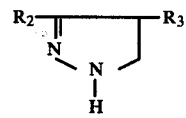

wherein $R_2$ and $R_3$ have the above-indicated meanings, with a compound of the formula

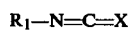

wherein $R_1$ and X also has the above-mentioned meaning.

The reaction is carried out at room temperature and in the presence of a solvent, for example on ether for example diethylether or petroleum ether.

The compounds in which $R_4$ is not a hydrogen atom can be prepared from the pyrazolines obtained in the above-described manner, in which $R_4=H$ according to methods which are known per se. Compounds in which $R_4$ is an alkyl group can be obtained, for example, by reacting the compound in which $R_4=H$ with an alkyl halide in a polar solvent in the presence of an acid binding agent.

Another method of preparing compounds in which $R_4$ is not a hydrogen atom is the reaction of a pyrazoline derivative which is not substituted in the 1 position with an $R_1$, $R_4$ disubstituted cabamoylchloride or $R_1$, $R_4$ disubstituted carbamic acid ester.

The above-mentioned starting material of the formula

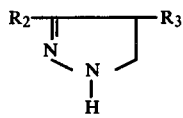

can be prepared in various manners dependent on the meaning of the substituents $R_2$ and $R_3$. Inter alia, when the substituents $R_2$ and $R_3$ are a substituted or nonsubstituted pyridyl group, thienyl group or phenyl group, the said starting material can be prepared by reacting a compound of the formula

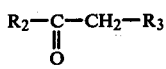

with formaldehyde in acid medium and in the presence of a solvent and a catalyst, so that a compound of the formula

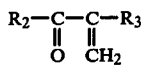

is obtained.

The reaction is carried out at elevated temperature, for example at the boiling point of the solvent used. Suitable solvents are, for example, alcohols, for example methanol. A useful catalyst is, for example piperidine.

The resulting product is then reacted with hydrazine in the presence of a solvent, for example an alcohol, for example propanol, a compound of the formula

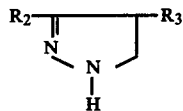

being obtained. The reaction is carried out at elevated temperature for example the boiling point of the solvent used.

The above-mentioned starting material can also be obtained by reacting a compound of the formula

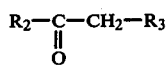

with dimethylamine and paraformaldehyde, a compound of the formula

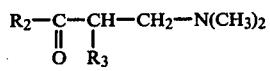

being formed. The reaction is carried out at elevated temperature in the presence of a solvent, for example ethanol. Upon prolonged heating, dimethylamine is usually split off again so that a compound of the formula

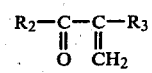

is obtained again.

The resulting products are then reacted with hydrazine at elevated temperature and in the presence of a solvent, for example ethanol, a compound of the formula

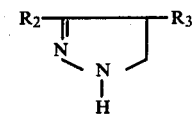

being obtained.

The invention will now be described in greater detail with reference to the following examples.

EXAMPLES

I. 1-(p-chlorophenylcarbamoyl)-3-(p-chlorophenyl)-4-(2-methoxyethyl) $\Delta^2$-pyrazoline.

(a) 10.6 g of dimethylaminohydrochloride, 4.0 g of paraformaldehyde and 21.3 g of 4'chloro-4-methoxybutyrophenone were suspended in 30 ml of dioxan. This mixture was then refluxed for 30 hours after which it was cooled. Dioxan was then evaporated for the greater part under reduced pressure. Water and ether were added to the residue, the ether layer was separated, washed with water and dried with sodium sulphate and evaporated. Yield 21.2 g of 2-(p-chlorobenzoyl)-4-methoxybutane-1.

(b) A solution of 21.1 g of 2-(p-chlorobenzoyl)-4-methoxybutene-1 and 10 ml of hydrazinehydrate in 50 ml of ethanol was boiled for 5 hours. After distillation, 12.3 g of 3-(p-chlorophenyl)-4-(2-methoxyethyl)-$\Delta^2$-pyrazoline were obtained. Boiling point (0.35-0.40 mm Hg): 155°-165° C.

(c) 7.7. g of p-chlorophenyl-isocyanate were added to the solution of 12 g of 3-(p-chlorophenyl)-4-(2-methoxyethyl)-$\Delta^2$-pyrazoline in 50 ml of dry ether. After stirring for 1 hour the ether was distilled off and replaced by 50 ml of petroleum ether. Stirring was continued for another 5 hours and the petroleum ether was sucked off. Yield 17.4 g of the compound mentioned in the title; m.p. 87° C.

In an analogous manner the following compounds were prepared:
1-(p-ethoxyphenylcarbamoyl)-3-(p-chlorophenyl)-4-(2-methoxyethyl)-$\Delta^2$-pyrazoline, m.p. 111° C.;
1-(p-methylthiophenylcarbamoyl)-3-(p-chlorophenyl)-4-(2-methoxyethyl)-$\Delta^2$-pyrazoline, m.p. 83° C.;
1-(p-nitrophenylcarbamoyl)-3-(p-chlorophenyl)-4-(2-methoxyethyl)-$\Delta^2$-pyrazoline, m.p. 159° C.;
1-cyclohexylcarbamoyl-3-(p-chlorophenyl)-4-(2-methoxyethyl)-$\Delta^2$-pyrazoline, m.p. 104° C.;

II. 1-(p-chlorophenylcarbamoyl)-3-(p-chlorophenyl)-4-(2-piperidinoethyl)-$\Delta^2$-pyrazoline.

(a) A suspension of 26.6 g of 4'-chloro-4-piperidinobutyrophenone, 4 g of paraformaldehyde and 10.6 g of dimethylamine-hydrochloride in 40 ml of dioxan was refluxed for 24 hours. After evaporation, water was added and the reaction mixture was rendered alkaline with 50% sodium hydroxide solution. After extracting with ether, washing with water, drying and evaporating 26.7 g of 1-(dimethylamino)-2-(p-chlorobenzoyl)-4-piperidinobutane were obtained.

(b) A solution of 26.7 g of the compound obtained according to (a) and 10 ml of hydrazinehydrate in 35 ml of ethanol were refluxed for 7 hours and then distilled. 18.1 g of 3-(p-chlorophenyl)-4-(2-piperidinoethyl)-Δ²-pyrazoline were obtained. Boiling point (0.4–0.5 mm Hg): 200°–208° C.;

(c) 15.4 g of p-chlorophenylisocyanate were added to a solution of 29.2 g of 3-(p-chlorophenyl)-4-(2-piperidinoethyl)-Δ²-pyrazoline in 500 ml of petroleum ether. The mixture was stirred for 12 hours and then sucked off. In this manner 36.4 g of the compound mentioned in the preamble was obtained; melting point 134° C.

The following compounds were prepared in an analogous manner:

1-cyclohexylcarbamoyl-3-(p-chlorophenyl)-4-(2-piperidinoethyl)-Δ²-pyrazoline, m.p. 113° C.;
1-(p-cyanophenylcarbamoyl)-3-(p-chlorophenyl)-4-(2-piperidinoethyl)-Δ²-pyrazoline, m.p. 148° C.;
1-(p-isopropoxyphenylcarbamoyl)-3-(p-chlorophenyl)-4-(2-piperidinoethyl)-Δ²-pyrazoline, m.p. 113° C.;
1-(p-ethylphenylcarbamoyl)-3-(p-chlorophenyl)-4-(2-piperidinoethyl)-Δ²-pyrazoline, m.p. 111° C.;
1-(p-chlorophenylcarbamoyl)-3-(p-chlorophenyl)-4-(2-diethylaminoethyl)-Δ²-pyrazoline, m.p. 100° C.;
1-(p-ethylphenylcarbamoyl)-3-(p-chlorophenyl)-4-(2-diethylaminoethyl)-Δ²-pyrazoline,
1-(p-isopropoxyphenylcarbamoyl)-3-(p-chlorophenyl)-4-(2-diethylaminoethyl)-Δ²-pyrazoline,
1-(p-cyanophenylcarbamoyl)-3-(p-chlorophenyl)-4-(2-diethylaminoethyl)-Δ²-pyrazoline,
1-cyclohexylcarbamoyl-3-(p-chlorophenyl)-4-(2-diethylaminoethyl)-Δ²-pyrazoline, m.p. 87° C.;
1-(p-chlorophenylcarbamoyl)-3-(p-chlorophenyl)-4-(2-phenylthioethyl)-Δ²-pyrazoline, m.p. 137° C.;
1-(p-isopropoxyphenylcarbamoyl)-3-(p-chlorophenyl)-4-(2-phenylthioethyl)-Δ²-pyrazoline, m.p. 138° C.;
1-(p-methylthiophenylcarbamoyl)-3-(p-chlorophenyl)-4-(2-phenylthioethyl)-Δ²-pyrazoline, m.p. 124° C.;
1-(p-ethylphenylcarbamoyl)-3-(p-chlorophenyl)-4-(2-phenylthioethyl)-Δ²-pyrazoline, m.p. 122° C.;
1-(p-fluorophenylcarbamoyl)-3-(p-chlorophenyl)-4-(2-phenylthioethyl)-Δ²-pyrazoline, m.p. 130° C.;

III. 1-(p-isopropoxyphenylcarbamoyl)-3-(p-chlorophenyl)-4-(2-phenoxyethyl)-Δ²-pyrazoline.

(a) A mixture of 27.5 g of 4'-chloro-4-phenoxybutyrophenone, 4 g of paraformaldehyde and 10.9 g of dimethylaminohydrochloride in 40 ml of dioxan was refluxed for 40 hours. After cooling, adding water and extracting with ether, the ether layer was separated, washed with water, dried and evaporated. In this manner 28.5 g of 2-(p-chlorobenzoyl)-4-phenoxybutene-1 were obtained.

(b) A solution of 28.5 g of the compound obtained according to (a) and 10 ml of hydrazinehydrate in 50 ml of ethanol was refluxed for 5 hours. The reaction mixture was then cooled and sucked off. In this manner 19 g of 3-(p-chlorophenyl)-4-(2-phenoxyethyl)-Δ²-pyrazoline were obtained.

(c) 1.8 g of isopropoxyphenylisocyanate were added to a solution of 3 g of the compound obtained according to (b) in 15 ml of ether. After stirring for 3 hours the reaction mixture was sucked off. In this manner 2.2 g of the compound mentioned in the title was obtained; m.p. 100° C.

The following compounds are prepared in a similar manner:

1-(p-methylthiophenylcarbamoyl)-3-(p-chlorophenyl)-4-(2-phenoxyethyl)-Δ²-pyrazoline, m.p. 112° C.;
1-(p-benzylphenylcarbamoyl)-3-(p-chlorophenyl)-4-phenyl-Δ²-pyrazoline, m.p. 179° C.;
1-(p-phenylthiophenylcarbamoyl)-3-(p-chlorophenyl)-4-phenyl-Δ²-pyrazoline, m.p. 164° C.;
1-(p-phenoxyphenylcarbamoyl)-3-(p-chlorophenyl)-4-phenyl-Δ²-pyrazoline, m.p. 177° C.;
1-[N-(p-chlorophenyl)-N-(trichloromethylthio)carbamoyl]-3-(p-chlorophenyl)-4-phenyl-Δ²-pyrazoline, m.p. 177° C.;
1-[N-benzyl-N-(p-chlorophenyl)-carbamoyl]-3-(p-chlorophenyl)-4-phenyl-Δ²-pyrazoline, m.p. 116° C.;
1-[N-cyclohexyl-N-(p-chlorophenyl)carbamoyl]-3-(p-chlorophenyl)-4-phenyl-Δ²-pyrazoline, m.p. 138° C.;

IV. The active compounds according to the invention are dispersed in water, and that in concentrations of 300; 100; 30; 10; 3; 1 and 0.3 mg of the active compound per liter of aqueous dispersion. The insecticidal activities of these dispersions were determined in the usual manner against *Leptinotarsa decemlineata* (Colorado beetle) and *Pieris brassicae* (cabbage worm). The results of these tests are recorded in the following table. The meanings of the characters used in the table are as follows:

+ = 90 to 100% mortality
± = 50 to 90% mortality
− = <50% mortality

TABLE

Biocidal activity against larvae of Leptinotarsa decemlineata and Pieres brassicae

| Compound number according to the aforementioned list | Biocidal activity concentration expressed in mg of active substance per liter (PPM) | | | | | | | | | | | | | |
|---|---|---|---|---|---|---|---|---|---|---|---|---|---|---|
| | Cola L | | | | | | | Pieris Brassicae | | | | | | |
| | 300 | 100 | 30 | 10 | 3 | 1 | 0,3 | 300 | 100 | 30 | 10 | 3 | 1 | 0,3 |
| 1 | ± | ± | − | | | | | − | | | | | | |
| 2 | + | + | ± | − | | | | + | + | − | | | | |
| 4 | + | + | + | + | + | | | − | | + | − | | | |
| 5 | + | + | + | + | − | | | + | + | ± | − | | | |
| 6 | + | + | ± | − | | | | + | + | − | | | | |
| 7 | + | ± | − | | | | | + | + | − | | | | |
| 10 | + | ± | − | | | | | + | + | ± | − | | | |
| 11 | + | + | + | ± | − | | | − | | | | | | |
| 12 | + | ± | − | | | | | + | + | − | | | | |
| 13 | ± | − | | | | | | + | + | ± | − | | | |
| 14 | ± | ± | − | | | | | − | | | | | | |
| 15 | ± | − | | | | | | + | − | | | | | |
| 16 | ± | − | | | | | | | | | | | | |

TABLE-continued
Biocidal activity against larvae of Leptinotarsa decemlineata and Pieres brassicae

| Compound number according to the aforementioned list | Biocidal activity concentration expressed in mg of active substance per liter (PPM) | | | | | | | | | | | | | |
|---|---|---|---|---|---|---|---|---|---|---|---|---|---|---|
| | Cola L | | | | | | | Pieris Brassicae | | | | | | |
| | 300 | 100 | 30 | 10 | 3 | 1 | 0,3 | 300 | 100 | 30 | 10 | 3 | 1 | 0,3 |
| 17 | ± | ± | − | | | | | + | ± | − | | | | |
| 21 | + | + | + | + | + | ± | − | + | + | − | | | | |
| 22 | + | + | + | ± | ± | ± | − | + | − | | | | | |
| 23 | + | + | + | ± | − | | | + | + | − | | | | |
| 24 | + | + | + | ± | − | | | + | + | − | | | | |
| 27 | + | + | ± | ± | − | | | + | + | + | + | ± | − | |
| 28 | + | + | + | + | − | | | + | + | + | + | − | | |
| 29 | + | + | + | + | + | ± | − | + | + | + | + | + | ± | − |
| 30 | + | + | + | + | ± | − | | + | + | + | + | + | + | − |
| 31 | + | + | + | + | ± | − | | + | + | + | + | + | − | |
| 32 | + | + | + | + | ± | − | | + | + | + | + | + | − | |
| 33 | + | + | + | + | − | | | + | + | + | + | ± | − | |
| 34 | + | + | + | + | − | | | + | + | + | + | − | | |
| 35 | + | + | + | ± | − | | | + | + | + | ± | | | |
| 36 | + | | | | | | | + | | | | | | |
| 37 | + | + | + | ± | − | | | + | + | − | | | | |
| 38 | + | + | ± | − | | | | + | − | | | | | |
| 39 | + | | | | | | | + | | | | | | |
| 40 | + | | | | | | | + | | | | | | |
| 41 | + | | | | | | | + | | | | | | |
| 42 | + | ± | − | | | | | + | − | | | | | |
| 43 | ± | | | | | | | + | | | | | | |
| 51 | + | + | + | ± | − | | | + | + | − | | | | |
| 52 | + | ± | − | | | | | + | + | − | | | | |
| 55 | + | | | | | | | + | | | | | | |
| 57 | + | + | ± | ± | − | | | + | + | − | | | | |
| 58 | + | | | | | | | + | | | | | | |
| 59 | + | + | + | ± | − | | | + | + | ± | − | | | |
| 60 | + | | | | | | | + | | | | | | |
| 61 | + | | | | | | | + | | | | | | |
| 62 | + | | | | | | | + | | | | | | |
| 63 | + | + | + | ± | − | | | + | + | + | + | ± | − | |
| 64 | | | | | | + | | | | | | | | |
| 65 | + | | | | | | | + | | | | | | |
| 66 | + | + | + | − | | | | + | + | + | + | ± | − | |
| 67 | + | | | | | | | + | | | | | | |
| 69 | + | + | ± | − | | | | + | + | + | + | − | | |
| 72 | ± | ± | − | | | | | + | + | + | − | | | |
| 74 | + | + | + | + | ± | − | | + | + | + | − | | | |
| 76 | + | + | − | | | | | + | + | − | | | | |
| 84 | + | + | ± | ± | − | − | | | | | | | | |
| 88 | + | + | + | ± | − | | | + | + | + | + | − | | |
| 89 | + | ± | ± | − | | | | + | + | + | − | | | |
| 91 | + | + | ± | ± | − | | | + | + | + | + | − | | |
| 94 | + | + | + | − | | | | + | + | + | − | | | |

What is claimed is:

1. A compound of the formula:

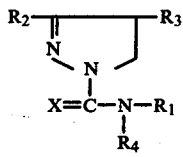

wherein $R_1$ is a member selected from the group consisting of alkyl of 1 to 4 carbon atoms, cycloalkyl of 3 to 6 carbon atoms, phenylalkyl wherein the alkyl moiety is of 1–4 carbon atoms, ring halogenated phenylalkyl wherein the alkyl moiety is of 1–4 carbon atoms, ring nitrated phenylalkyl wherein the alkyl moiety is of 1–4 carbon atoms, ring alkylated phenylalkyl wherein the alkyl moiety is of 1–4 carbon atoms, phenyl, phenyl substituted in the 2, 3 or 4 positions with up to two substituents selected from the group consisting of halogen, alkyl of 1 to 4 carbon atoms, halogenated alkyl of 1 to 4 carbon atoms, cycloalkyl of 3 to 6 carbon atoms, alkylthio of 1 to 4 carbon atoms, alkoxy of 1 to 4 carbon atoms, dialkylamino wherein each alkyl moiety is of 1 to 4 carbon atoms, alkylsulfonyl of 1 to 4 carbon atoms, acyl of an aliphatic saturated monocarboxylic acid, acylamino wherein the acyl moiety is of an aliphatic saturated monocarboxylic acid, nitro, phenyl, halogenated phenyl and cyano, $R_2$ is a member selected from the group consisting of alkyl of 1 to 4 carbon atoms, cycloalkyl of 3 to 6 carbon atoms, phenyl, phenyl substituted with 1 to 2 substituents selected from the group consisting of halogen, alkyl of 1 to 4 carbon atoms, haloalkyl of 1 to 4 carbon atoms, cycloalkyl of 3 to 6 carbon atoms, alkylthio of 1 to 4 carbon atoms, alkoxy of 1 to 4 carbon atoms, monoalkylamino of 1 to 4 carbon atoms, dialkylamino wherein each alkyl is of 1 to 4 carbon atoms, nitro, phenyl, halophenyl and cyano, pyridyl, thienyl, halothienyl, nitrothienyl and alkyl substituted thienyl wherein the alkyl is of 1 to 4 carbon atoms, $R_3$ is a member selected from the group consisting of alkyl of 5 to 10 carbon atoms, alkyl of 1 to 6 carbon atoms substituted with a moiety selected from the group consisting of cycloalkyl of 3 to 6 carbon atoms, alkoxy of 1 to 4 carbon atoms, alkylthio of 1 to 4 carbon atoms, nitro, piperidino, N-methyl-piperazino, halo, cyano, alkoxycarbonyl of 1 to 4 carbon atoms, nitrophenyl, halophenyl, alkyl substituted phenyl wherein the alkyl is of 1 to 4 carbon atoms, phenoxy, phenylthio, phenylsulfenyl, phenylsulfonyl, alkylphenylamino wherein the alkyl is of 1 to 4 carbon atoms, diphenylamino, dialkylamino wherein each alkyl is of 1 to 4 carbon atoms, N,N-dialkylcarbamoyl wherein each alkyl is of 1 to 4 carbon atoms and N,N-dialkylsulfamoyl wherein each alkyl is of 1 to 4 carbon atoms, $R_4$ is a member selected from the group consisting of hydrogen, alkyl of 1 to 15 carbon atoms, phenylalkyl wherein the alkyl is of 1 to 4 carbon atoms, cycloalkyl of 3 to 6 carbon atoms and halomethylthio and X is a member selected from the group consisting of oxygen and sulfur and with the proviso that when $R_1$ is phenyl substituted with a moiety selected from the group consisting of phenylthio, phenoxy and phenylalkyl and/or $R_4$ is a moiety selected from the group consisting of phenylalkyl, cycloalkyl and halomethylthio $R_3$ may in addition be a member selected from the group as $R_2$.

2. The compound of claim 1 wherein $R_3$ is alkyl of 1 to 6 carbon atoms substituted with a member selected from the group consisting of alkoxy of 1 to 4 carbon atoms and dialkylamino wherein each alkyl is of 1 to 4 carbon atoms.

3. The compound of claim 1 wherein $R_3$ is alkyl of 1 to 6 carbon atoms substituted with piperidino or with N-methylpiperazino.

4. 1-(4-chlorophenylcarbamoyl)-3-(4-chlorophenyl)-4-(2-methoxyethyl)-2-pyrazoline, m.p. 87° C.

5. 1-(4-ethoxyphenylcarbamoyl)-3-(4-chlorophenyl)-4-(2-methoxyethyl)-2-pyrazoline, m.p. 111° C.

6. 1-(4-methylthiophenylcarbamoyl)-3-(4-chlorophenyl)-4-(2-methoxyethyl)-2-pyrazoline, m.p. 83° C.

7. 1-(4-nitrophenylcarbamoyl)-3-(4-chlorophenyl)-4-(2-methoxyethyl)-2-pyrazoline, m.p. 159° C.

8. 1-(4-cyanophenylcarbamoyl)-3-(4-chlorophenyl)-4-(2-piperidinoethyl)-2-pyrazoline, m.p. 148° C.

9. 1-(4-isopropoxyphenylcarbamoyl)-3-(4-chlorophenyl)-4-(2-piperidinoethyl)-2-pyrazoline, m.p. 113° C.

10. 1-(4-ethylphenylcarbamoyl)-3-(4-chlorophenyl)-4-(2-piperidinoethyl)-2-pyrazoline, m.p. 111° C.

11. 1-(4-chlorophenylcarbamoyl)-3-(4-chlorophenyl)-4-(2-piperidinoethyl)-2-pyrazoline, m.p. 134° C.

12. 1-(4-chlorophenylcarbamoyl)-3-(4-chlorophenyl)-4-(2-diethylaminoethyl)-2-pyrazoline, m.p. 100° C.

13. 1-(4-ethylphenylcarbamoyl)-3-(4-chlorophenyl)-4-(2-diethylaminoethyl)-2-pyrazoline.

14. 1-(4-isopropoxyphenylcarbamoyl)-3-(4-chlorophenyl)-4-(2-diethylaminoethyl)-2-pyrazoline.

15. 1-(4-cyanophenylcarbamoyl)-3-(4-chlorophenyl)-4-(2-diethylaminoethyl)-2-pyrazoline.

16. 1-cyclohexylcarbamoyl-3-(4-chlorophenyl)-4-(2-diethylaminoethyl)-2-pyrazoline, m.p. 87° C.

17. An insecticidal composition comprising a compound of claim 1 in an insecticidally effective amount and a finely divided carrier therefore.

18. A method of controlling insects in agriculture and horticulture comprising treating areas effected with said insects with the composition of claim 17 in an amount corresponding to 0.05–1 kg of compound per hectare.

* * * * *